US009642858B2

(12) United States Patent
Horzempa et al.

(10) Patent No.: US 9,642,858 B2
(45) Date of Patent: May 9, 2017

(54) USE OF RESAZURIN, OR ANALOGS THEREOF, FOR ANTIBACTERIAL THERAPY

(71) Applicants: Joseph Andrew Horzempa, Pittsburgh, PA (US); Dawn Marie Henson, Pittsburgh, PA (US); Gerard Joseph Nau, Sewickley, PA (US)

(72) Inventors: Joseph Andrew Horzempa, Pittsburgh, PA (US); Dawn Marie Henson, Pittsburgh, PA (US); Gerard Joseph Nau, Sewickley, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/439,651

(22) PCT Filed: Oct. 29, 2013

(86) PCT No.: PCT/US2013/067296
§ 371 (c)(1),
(2) Date: Apr. 29, 2015

(87) PCT Pub. No.: WO2014/070760
PCT Pub. Date: May 8, 2014

(65) Prior Publication Data

US 2015/0258103 A1 Sep. 17, 2015

Related U.S. Application Data

(60) Provisional application No. 61/720,254, filed on Oct. 30, 2012.

(51) Int. Cl.
*A61K 31/535* (2006.01)
*A61K 31/5415* (2006.01)
*A61K 31/538* (2006.01)

(52) U.S. Cl.
CPC ........ *A61K 31/5415* (2013.01); *A61K 31/538* (2013.01)

(58) Field of Classification Search
CPC .................................................. A61K 31/538
(Continued)

(56) References Cited

U.S. PATENT DOCUMENTS 4,582,795 A * 4/1986 Shibuya .................. C12Q 1/04 422/430
4,719,094 A 1/1988 Rieckert et al.
(Continued)

FOREIGN PATENT DOCUMENTS

EP 1242614 9/2004
EP 2245176 8/2012

OTHER PUBLICATIONS

International Search Report and Written Opinion from International PCT/US2013/067296, dated Jan. 29, 2014, 10pp.
(Continued)

*Primary Examiner* — Shengjun Wang
(74) *Attorney, Agent, or Firm* — Klarquist Sparkman, LLP

(57) ABSTRACT

A method for treating infection by bacteria in a subject, comprising administering to the subject a therapeutically effective amount of resazurin or a resazurin analog, or a pharmaceutically acceptable salt or ester thereof, wherein the bacteria is selected from at least one of *Francisella* sp. or *Neisseria* sp.

17 Claims, 15 Drawing Sheets

Figure 2:
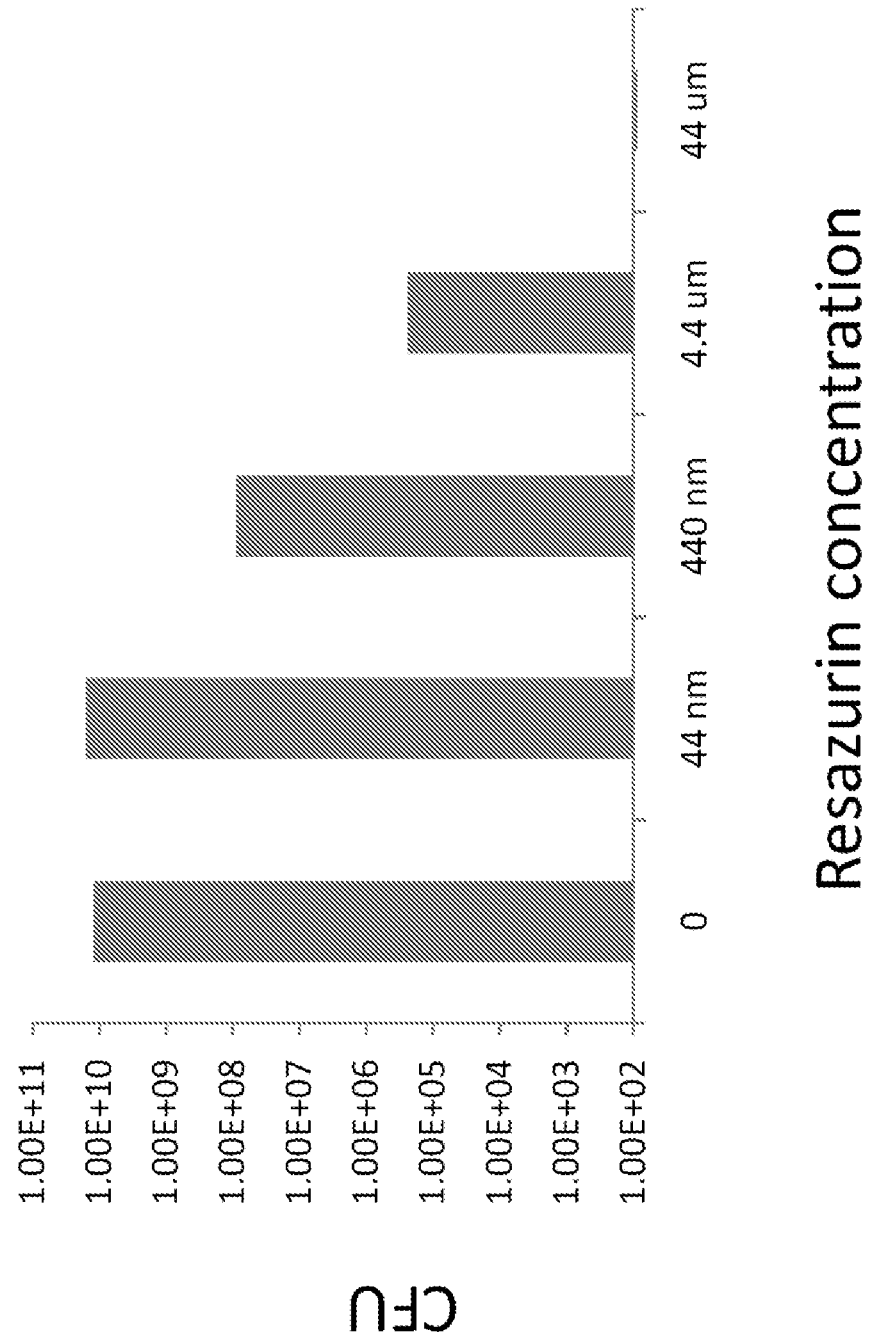

| Bacterial Strain | choc | choc 44 μM Res |
|---|---|---|
| *Francisella tularensis* Schu S4 | + | - |
| *F. tularensis* LVS | + | - |
| *F. novicida* | + | - |
| *F. philomoragia* | + | + |
| *Neisseria gonorrhoeae* | + | - |
| *N. polysaccharea* | + | - |
| *N. sicca* | + | - |
| *Acinetobacter baumannii* 122 | + | + |
| *A. baumannii* 19606 | + | + |
| *A. baumannii* 17978 | + | + |
| *Pseudomonas aeruginosa* 1244 | + | + |
| *Escherichia coli* BL21 | + | + |
| *Salmonella typhimurium* LT2 | + | + |
| *Staphylococcus aureus* | + | + |
| *Listeria monocytogenes* | + | + |
| *Klebsiella* sp. | + | + |
| *Streptococcus pneumoniae* | + | + |

(58) Field of Classification Search
USPC .................................................. 514/229.8
See application file for complete search history.

(56) References Cited

U.S. PATENT DOCUMENTS

| | | | |
|---|---|---|---|
| 4,834,042 | A | 5/1989 | Wakasa et al. |
| 4,954,630 | A | 9/1990 | Klein et al. |
| 5,304,645 | A | 4/1994 | Klein et al. |
| 5,501,959 | A | 3/1996 | Lancaster et al. |
| 7,432,372 | B2 | 10/2008 | Batchelor et al. |
| 8,017,606 | B2 | 9/2011 | Andries et al. |
| 2003/0086916 | A1* | 5/2003 | Goligorsky ............ A61K 31/00 424/94.4 |
| 2011/0015137 | A1* | 1/2011 | Cottarel ............ A61K 31/4745 514/21.1 |
| 2011/0086341 | A1 | 4/2011 | Batchelor et al. |
| 2011/0177605 | A1 | 7/2011 | Unkrig et al. |

OTHER PUBLICATIONS

Karuppusamy et al., "High Throughput Antibacterial Screening of Plant Extracts by Resazurin Redox with Special Reference to Medicinal Plants of Western Ghats," *Global Journal of Pharmacology*, 3(2): 63-68, 2009.

Drummond et al., "The development of microbiological methods for phytochemical screening," *Recent Research Developments in Phytochemistry*, 4: 143-152, 2000. (Abstract only).

Sridharan, V. et al., "One-pot synthesis of symmetrically disubstituted 3H-phenoxazin-3-ones by selective oxidative condensation with LTA," *Journal of Heterocyclic Chemistry*, 44: 491-493, 2007.

Wauven et al., "Pseudomonas aeruginosa mutants affected in anaerobic growth on arginiae: evidence for a four-gene cluster encoding the arginine deiminase pathway," *Journal of Bacteriology*, 160(3): 928-934, 1984.

Schmitt et al., "Antibacterial activity of resazurin-based compounds against *Neisseria gonorrhoeae* in vitro and in vivo," *International Journal of Antimicrobial Agents*, Jul. 19, 2016.

* cited by examiner

FIG. 1

| Bacterial Strain | choc | choc 44 µM Res |
|---|---|---|
| *Francisella tularensis* Schu S4 | + | - |
| *F. tularensis* LVS | + | - |
| *F. novicida* | + | - |
| *F. philomoragia* | + | + |
| *Neisseria gonorrhoeae* | + | - |
| *N. polysaccharea* | + | - |
| *N. sicca* | + | - |
| *Acinetobacter baumannii* 122 | + | + |
| *A. baumannii* 19606 | + | + |
| *A. baumannii* 17978 | + | + |
| *Pseudomonas aeruginosa* 1244 | + | + |
| *Escherichia coli* BL21 | + | + |
| *Salmonella typhimurium* LT2 | + | + |
| *Staphylococcus aureus* | + | + |
| *Listeria monocytogenes* | + | + |
| *Klebsiella* sp. | + | + |
| *Streptococcus pneumoniae* | + | + |

FIG. 9

*F. tularensis* LVS

Log₁₀ CFU/ml vs Resazurin (μM)

ered even more vulnerable to the consequences of bioterrorism.

USE OF RESAZURIN, OR ANALOGS THEREOF, FOR ANTIBACTERIAL THERAPY

CROSS REFERENCE TO RELATED APPLICATIONS

This is the U.S. National Stage of International Application No. PCT/US2013/067296, filed Oct. 29, 2013, which was published in English under PCT Article 21(2), which in turn claims the benefit of the earlier filing date of U.S. Provisional Application No. 61/720,254, filed Oct. 30, 2012. The entire disclosure of the prior applications are considered to be part of the disclosure of the accompanying application and are incorporated herein by reference.

BACKGROUND

*Neisseria* is a genus of Gram (−) bacteria included among the proteobacteria, a large group of Gram-negative bacteria. *Neisseria* are diplococci and the genus includes the species *N. gonorrhoeae* (also called the gonococcus), which causes gonorrhea, and *N. meningitidis* (also called the meningococcus), one of the most common causes of bacterial meningitis and the causative agent of meningococcal septicaemia. There are over 100 million new cases of gonorrhea annually, making *N. gonorrhoeae* the second most common sexually transmitted infectious bacterium. A closely related organism, *N. meningitidis* can cause a number of diseases, such as meningitis, fulminant septicemia, and bacteremia. Antimicrobial resistance and decreasing susceptibility of *Neisseria* species to extended-spectrum drugs has underscored the need for the development of new antibiotics that target pathogenic organisms in this genus.

*Francisella* is a genus of Gram (−) bacteria that are coccobacillary or rod-shaped, non-motile organisms, which are also facultative intracellular parasites of macrophages. *F. tularensis* causes tularemia (also known as rabbit fever). *F. novicida* and *F. philomiragia* are associated with septicemia and invasive systemic infections. The preferred course of treatment for tularemia is antibiotic therapy. *F. tularensis* is naturally resistant to β-lactam antibiotics such as penicillin. Aminoglycosides, such as gentamicin and streptomycin are effective, but are only used in severe cases because these drugs are nephrotoxic. Alternatively, members of the fluoroquinolone or tetracycline drug families can be used to treat tularemia. However, there is a high incidence of relapse (up to 15%) and treatment failures when using these drugs. *F. tularensis* is a highly infectious and deadly pathogen, and is classified by the CDC as a Category A bioterrorism agent. Inhalation of a single bacterium results in an acute pneumonia with a 30-60% mortality rate without treatment. The intentional development and release of antibiotic resistant strains of *F. tularensis* could be disastrous. Since a vaccine against tularemia licensed for human use does not exist, we are even more vulnerable to the consequences of bioterrorism.

SUMMARY

One embodiment disclosed herein relates to a method for treating infection by bacteria in a subject, comprising administering to the subject a therapeutically effective amount of resazurin or a resazurin analog, or a pharmaceutically acceptable salt or ester thereof, wherein the bacteria is selected from at least one of *Francisella* sp. or *Neisseria* sp.

Another embodiment disclosed herein relates to a method for inhibiting bacteria growth, comprising contacting an effective amount of resazurin or a resazurin analog, or a pharmaceutically acceptable salt or ester thereof, with at least one of *Francisella* sp. or *Neisseria* sp.

A further embodiment disclosed herein relates to a method for inhibiting the growth of at least one of *Francisella* sp. or *Neisseria* sp. on a substrate, comprising contacting the substrate with resazurin or a resazurin analog, or a pharmaceutically acceptable salt or ester thereof.

Also disclosed herein is an antibacterial composition comprising resazurin or a resazurin analog, or a pharmaceutically acceptable salt or ester thereof, and at least one pharmaceutically acceptable additive.

The foregoing will become more apparent from the following detailed description, which proceeds with reference to the accompanying figures.

BRIEF DESCRIPTION OF THE DRAWINGS

FIG. 1 is a graph showing the results of testing resazurin against several bacteria species.

FIG. 2 is a graph indicating that *F. tularensis* growth is inhibited by resazurin.

FIG. 3 is a graph indicating that resazurin is bactericidal to *F. tularensis*.

FIG. 4 is a graph indicating that resazurin reduces bacterial burden during infection of HEK-293 cells.

FIG. 5 is a graph indicating that resazurin reduces bacterial burden during infection of primary human macrophages.

FIG. 6 is a graph indicating that resazurin and resorufin are bactericidal to *F. tularensis*.

FIG. 7 is a graph indicating that resazurin does not have an antimicrobial effect on *Escherichia coli*.

FIG. 8 is a graph indicating that resazurin does not have an antimicrobial effect on *Pseudomonas aeruginosa*.

FIG. 9 is a graph indicating that the minimal inhibitory concentration of resazurin against *F. tularensis* is 4.4 μM.

FIG. 10 is a graph indicating that resorufin exhibits a similar antimicrobial effect to that of resazurin against *F. tularensis*.

FIG. 11 is a flow chart of the planned infection and treatment regimen for an in vivo experiment designed to show that resazurin and resorufin are effective therapies for *F. tularensis*.

FIG. 12 is a flow chart of the planned infection and treatment regimen for an in vivo experiment designed to show that resazurin and resorufin are effective therapies for *N. gonorrhoeae*.

FIG. 13 is a graph indicating the bacterial activity of resazurin and resorufin.

FIG. 14 is a graph indicating the rate of conversion of resazurin to resorufin in broth culture, by *F. tularensis* LVS.

FIG. 15 is a graph comparing the bacterial activity of resazurin and resorufin against *F. tularensis* LVS.

DETAILED DESCRIPTION

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration of" and "administering a" compound or agent should be understood to mean providing a compound or agent, a prodrug of a compound or agent, or a pharmaceutical composition as described herein. The compound, agent or composition can be administered by another person to the subject (e.g., intravenously) or it can be self-administered by the subject (e.g., tablets).

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$)alkoxy can be methoxy, ethoxy, propoxy, isopropoxy, butoxy, isobutoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$) alkanoyl can be acetyl, propanoyl or butanoyl; halo($C_1$-$C_6$) alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; ($C_1$-$C_6$)alkylthio can be methylthio, ethylthio, propylthio, isopropylthio, butylthio, isobutylthio, pentylthio, or hexylthio; ($C_2$-$C_6$) alkanoyloxy can be acetoxy, propanoyloxy, butanoyloxy, isobutanoyloxy, pentanoyloxy, or hexanoyloxy.

The term "alkylaryl" refers to a group in which an alkyl group is substituted for a hydrogen atom of an aryl group. An example is —Ar—R, wherein Ar is an arylene group and R is an alkyl group.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

The term "amine" or "amino" refers to a group of the formula —NRR', where R and R' can be, independently, hydrogen or an alkyl, alkenyl, alkynyl, aryl, aralkyl, carbonyl (e.g., —C(O)R'', where R'' can be hydrogen, an alkyl, alkenyl, alkynyl, aryl, or an aralkyl), cycloalkyl, halogenated alkyl, or heterocycloalkyl group. For example, an "alkylamino" or "alkylated amino" refers to —NRR', wherein at least one of R or R' is an alkyl.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —C(O)—N(R) (wherein R is a substituted group or H). An "aminocarbonyl" is inclusive of an amido group. A suitable aminocarbonyl group is acetamido.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. Structural analogs are often found using quantitative structure activity relationships (QSAR), with techniques such as those disclosed in Remington (*The Science and Practice of Pharmacology*, 19th Edition (1995), chapter 28). A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "antibacterial" will thus be used herein to refer to a material or agent that kills or otherwise inhibits the growth of bacterial organisms.

An "antibacterial effective amount" is an amount of an antibacterial component or mixture of components that is sufficient to inhibit the growth of at least one bacteria in a sample to a statistically significant degree, preferably by at least about 25%, more preferably by at least about 50%, and most preferably completely inhibiting growth of the bacteria, compared to a control sample lacking the antimicrobial component.

The term "aralkyl" refers to an alkyl group that has at least one hydrogen atom replaced by an aryl group. An example of an aralkyl group is a benzyl group.

The term "aryl" refers to any carbon-based aromatic group including, but not limited to, phenyl, naphthyl, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

The term "co-administration" or "co-administering" refers to administration of at least two therapeutic compounds or agents within the same general time period, and does not require administration at the same exact moment in time (although co-administration is inclusive of administering at the same exact moment in time). Thus, co-administration may be on the same day or on different days, or in the same week or in different weeks. The therapeutic agents or compounds may be included in the same composition or they may each individually be included in separate compositions. In certain embodiments, the therapeutic agents or compounds agents may be administered during a time frame wherein their respective periods of biological activity overlap. Thus, the term includes sequential as well as coextensive administration of two or more agents.

"Derivative" refers to a compound or portion of a compound that is derived from or is theoretically derivable from a parent compound.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition "Inhibiting" also refers to any quantitative or qualitative reduction in biological activity or binding, relative to a control "Inhibiting" also include slowing or stopping the growth or proliferation of certain bacteria for a certain period of time.

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

The term "subject" includes both human and veterinary subjects.

A "therapeutically effective amount" or "diagnostically effective amount" refers to a quantity of a specified agent sufficient to achieve a desired effect in a subject being treated with that agent. Ideally, a therapeutically effective amount or diagnostically effective amount of an agent is an amount sufficient to inhibit or treat the disease without causing a substantial cytotoxic effect in the subject. The therapeutically effective amount or diagnostically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is substituted (e.g. substituted aryl). In some embodiments, the number of substituted groups linked together is limited to two (e.g. substituted alkyl is substituted with substituted aryl, wherein the substituent present on the aryl is not further substituted). In some embodiments, a substituted group is not substituted with another substituted group (e.g. substituted alkyl is substituted with unsubstituted aryl).

Agents

Resazurin, and analogs thereof, may be used as a novel antibiotic against bacteria, particularly pathogenic bacteria such as *F. tularensis* and *Neisseria* spp. Resazurin (7-Hydroxy-3H-phenoxazin-3-one 10-oxide) is a nontoxic blue dye commonly used in mammalian cell cultures as an indicator for cell viability and to assess metabolic activity. Reduction of resazurin leads to resorufin in mammalian cells.

The resazurin or a resazurin analog, or a pharmaceutically acceptable salt or ester thereof, may have a structure of formula I:

wherein $R^a$ represents H, substituted or unsubstituted alkyl, substituted or unsubstituted aryl, O, and $C(X^a)R^{a1}$, in which $X^a$ represents O, S or NH and $R^{a1}$ is a member selected from substituted or unsubstituted alkyl, substituted or unsubstituted heteroalkyl, substituted or unsubstituted aryl, substituted or unsubstituted heteroaryl, substituted or unsubstituted heterocycloalkyl, substituted or unsubstituted acyl, $OR^{a2}$ and $NR^{a3}R^{a4}$, wherein $R^{a2}$, $R^{a3}$ and $R^{a4}$ each independently represent moieties such as hydrogen, substituted alkyl, unsubstituted alkyl, substituted heteroalkyl, unsubstituted heteroalkyl, substituted heterocycloalkyl, unsubstituted heterocycloalkyl, substituted carboxyalkyl, unsubstituted carboxyalkyl, substituted sulfoalkyl, unsubstituted sulfoalkyl, substituted acyl, unsubstituted acyl, substituted haloalkyl, unsubstituted haloalkyl, substituted alkoxy, or unsubstituted alkoxy;

"n" represents either 0 or 1;

X is oxygen or sulfur;

$R^b$, $R^c$, $R^e$, $R^f$, $R^h$ and $R^i$ are each independently selected from H, OH, sulfo, nitro, carboxyl, carboxylate esters, halogen, substituted or unsubstituted alkyl, substituted or unsubstituted heteroalkyl (e.g., alkoxy, alkylthio, aminoalkyl, etc.), substituted or unsubstituted aryl, substituted or unsubstituted heteroaryl, substituted or unsubstituted heterocycloalkyl;

$R^d$ represents $OR^{d1}$ or $NR^{d1}R^{d2}$, wherein the identities of $R^{d1}$ and $R^{d2}$ are the same as those set forth for $R^{a1}$, $R^{a3}$ and $R^{a4}$; and $R^g$ represents $OR^{g1}$, $NR^{g1}R^{g2}$ or (=O), wherein the identities of $R^{g1}$ and $R^{g2}$ are the same as those set forth above for $R^{d1}$ and $R^{d2}$.

The dashed lines in the formula represent double bonds that are either present or absent as required to satisfy the rules of valency.

In certain embodiments, the resazurin analog is resorufin or a resorufin analog having a structure of formula II:

wherein $R^2$, $R^3$, $R^4$, $R^5$, $R^6$ and $R^7$ each independently represent hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, or hydroxyl;

A is $OR^8$ or $NR^9R^{10}$;

Z is either O or quaternized amine, $N^+R^9R^{10}$;

X is oxygen or sulfur;

$R^8$ is an alkyl, an aralkyl, an alkylaryl, or hydrogen; and $R^9$ and $R^{10}$ are each independently represent hydrogen, halogen, substituted alkyl, unsubstituted alkyl, substituted alkoxy, unsubstituted alkoxy, substituted alkylthio, unsubstituted alkylthio, substituted aryl, unsubstituted aryl, substituted heteroaryl, unsubstituted heteroaryl, sulfo, nitro, carboxyl, or hydroxyl. In certain embodiments, X is oxygen and Z is oxygen. In other embodiments, X is oxygen, Z is oxygen, $R^2$, $R^3$, $R^4$, $R^5$, $R^6$ and $R^7$ each independently represent hydrogen, and A is $OR^8$ (wherein $R^8$ is H in one embodiment, or $R^8$ is $C_1$-$C_6$ alkyl, aralkyl, or alkylaryl such as benzyl, pentyl, methyl or ethyl).

More specific embodiments of the resorufin or resorufin analog have a structure of formula III:

wherein $R^2$, $R^3$, $R^4$, $R^5$, $R^6$, $R^7$ and X are the same as in formula II. In preferred embodiments, X is O.

A more specific embodiment of resazurin or a resazurin analog has a structure of formula IV:

wherein $R^2$, $R^3$, $R^4$, $R^5$, $R^6$, $R^7$, A, Z and X are the same as in formula II. In preferred embodiments, X is O and Z is O.

The agents disclosed herein may be prepared by synthetic approaches known in the art.

Pharmaceutical Compositions and Method of Use

A. Overview

Figure 3:
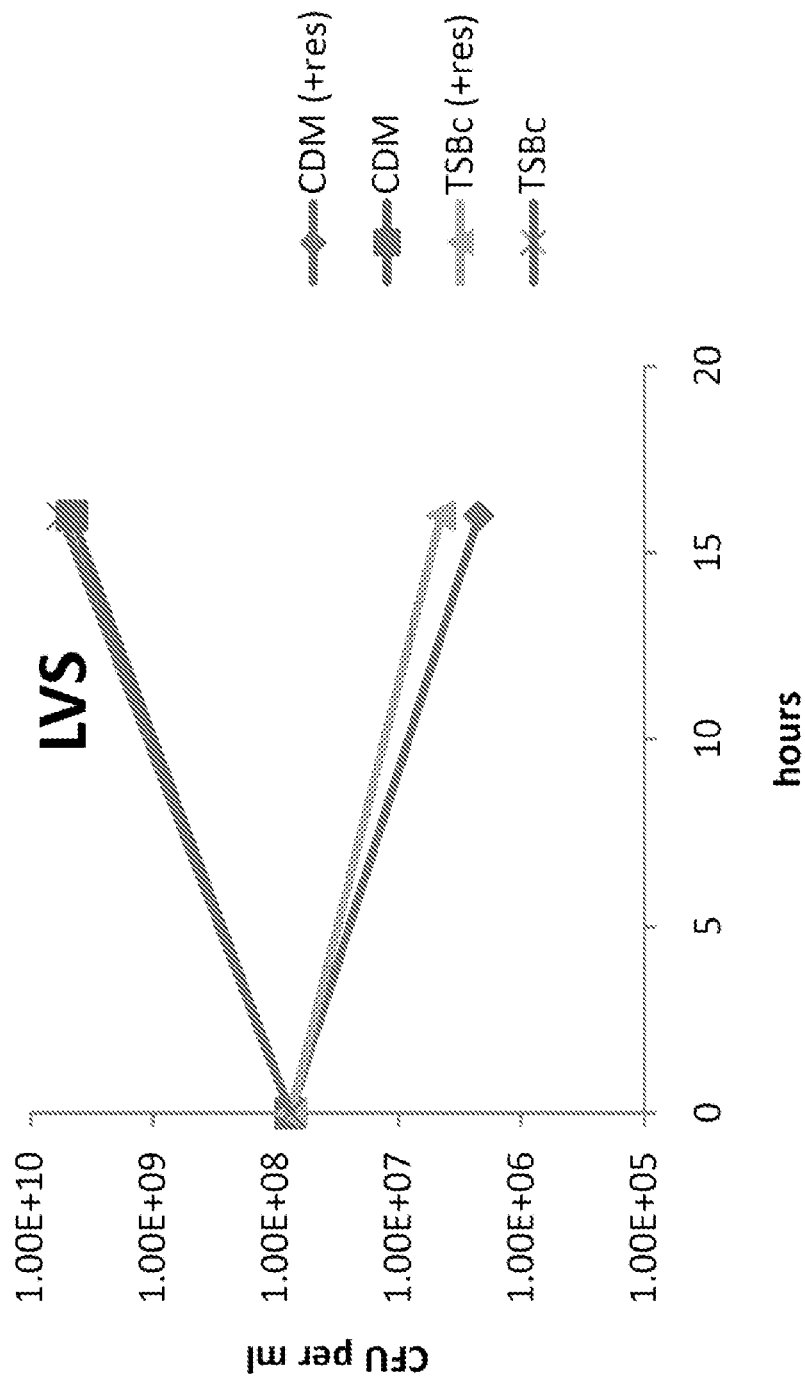
Figure 7:
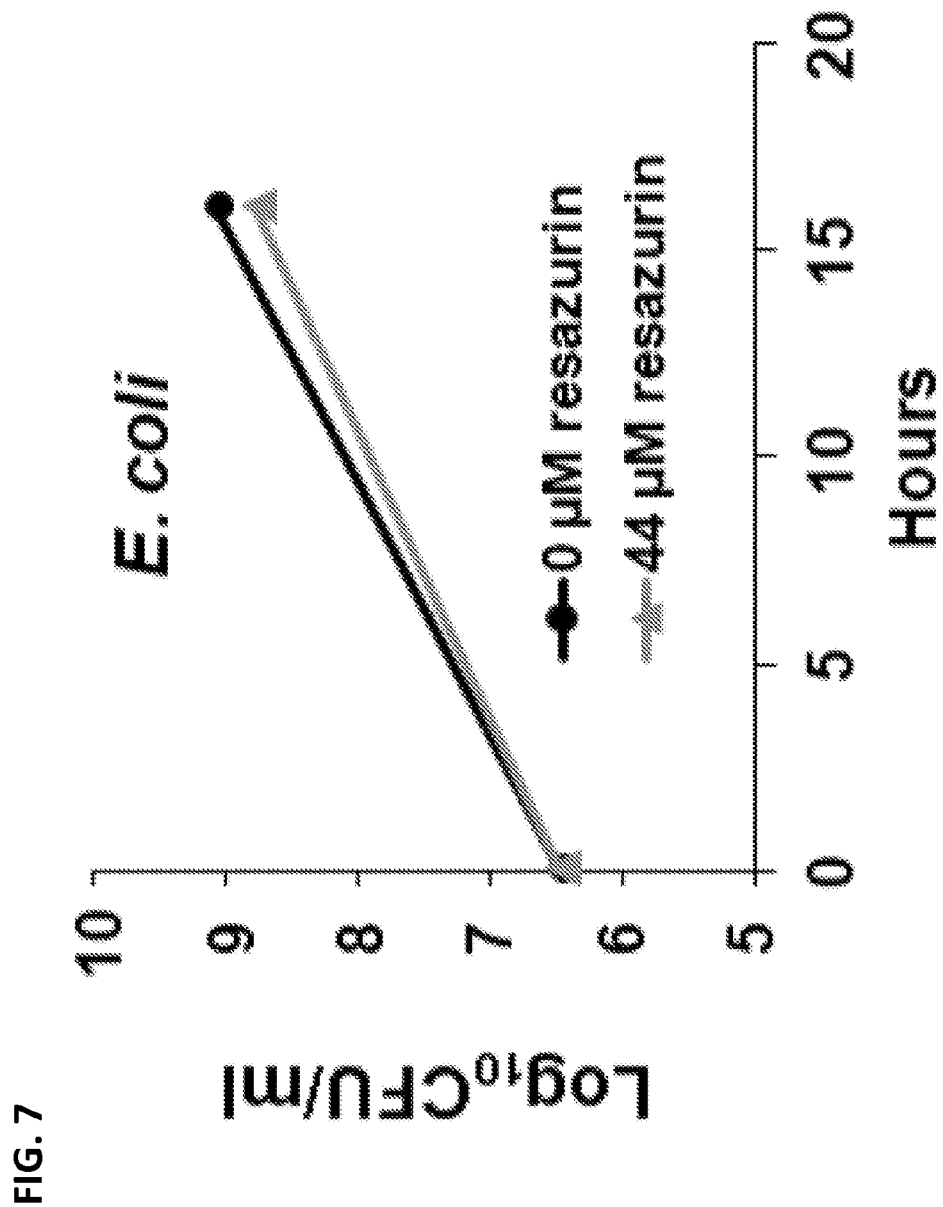
Figure 8:
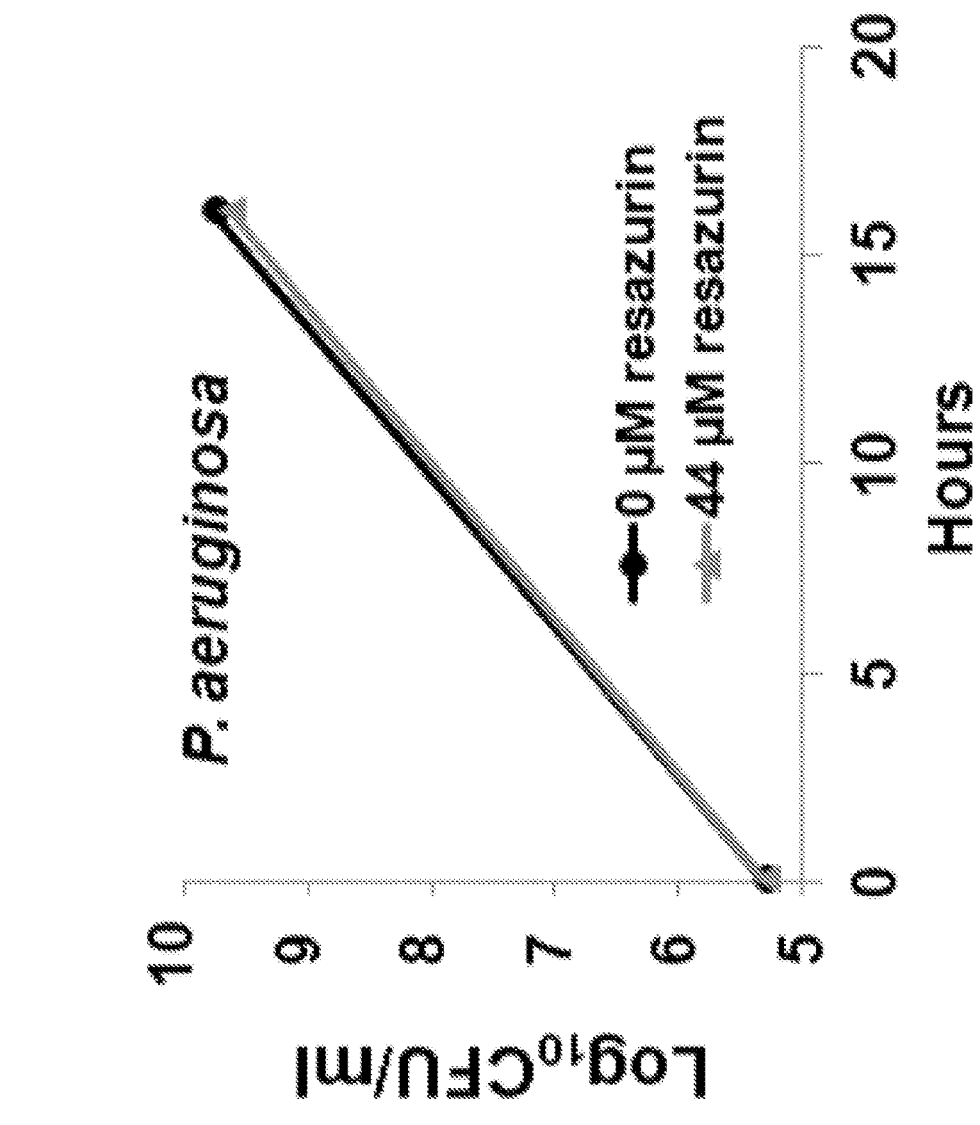
Figure 9:
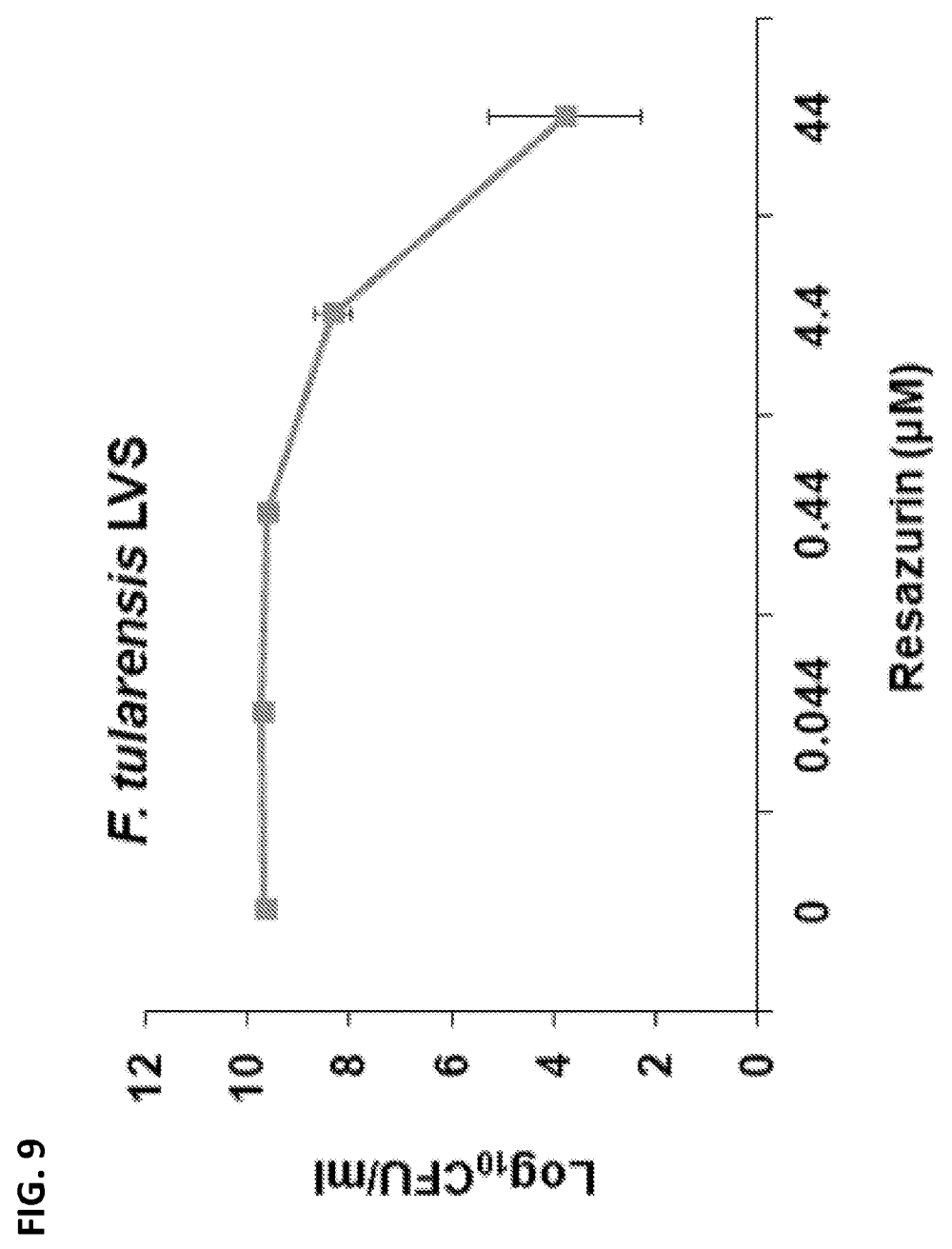

Resazurin is commonly used to monitor growth and viability of bacterial, and other, cell types. However, surprisingly, the inclusion of resazurin in cultures of *F. tularensis* LVS (live vaccine strain) at the concentration recommended by the manufacturer (44 µM; concentration for Alamar blue reagent) resulted in a decrease in viable bacteria (FIG. 3). However, inclusion of 44 µM resazurin in *Escherichia coli* or *Pseudomonas aeruginosa* cultures had no effect on bacterial viability, as expected (FIGS. 7 and 8). This indicated that the antibacterial effect of resazurin on *F. tularensis* may be specific to this bacterium, or to a subset of bacterial species. Further tests were prepared on chocolate II agar plates with or without 44 µM resazurin and these were inoculated with an assortment of bacteria from diverse taxa (FIG. 1). At this concentration, a potent bactericidal effect was observed against various *F. tularensis* and *Neisseria* species, including the human pathogens type A *F. tularensis* (Schu S4) and *N. gonorrhoeae*. Lowering the resazurin concentration to as little as about 4.4 µM still resulted in about a 10-fold reduction in viable *F. tularensis* LVS bacteria compared to growth medium alone (FIGS. 2 and 9). (This would be equivalent to a dose of approximately 1 mg/kg in an animal model.) To ensure that this was not an effect of the medium, the test were repeated in both Trypicase soy broth supplemented with 0.1% cysteine HCL (TSBc) and Chamberlain's chemically defined medium (CDM) (Chamberlain, R. E. 1965. Evaluation of live tularemia vaccine prepared in a chemically defined medium. *Appl. Microbiol.* 13, 232-235). The results indicated that the antimicrobial activity was not affected by the choice of medium (FIG. 3).

Figure 14:
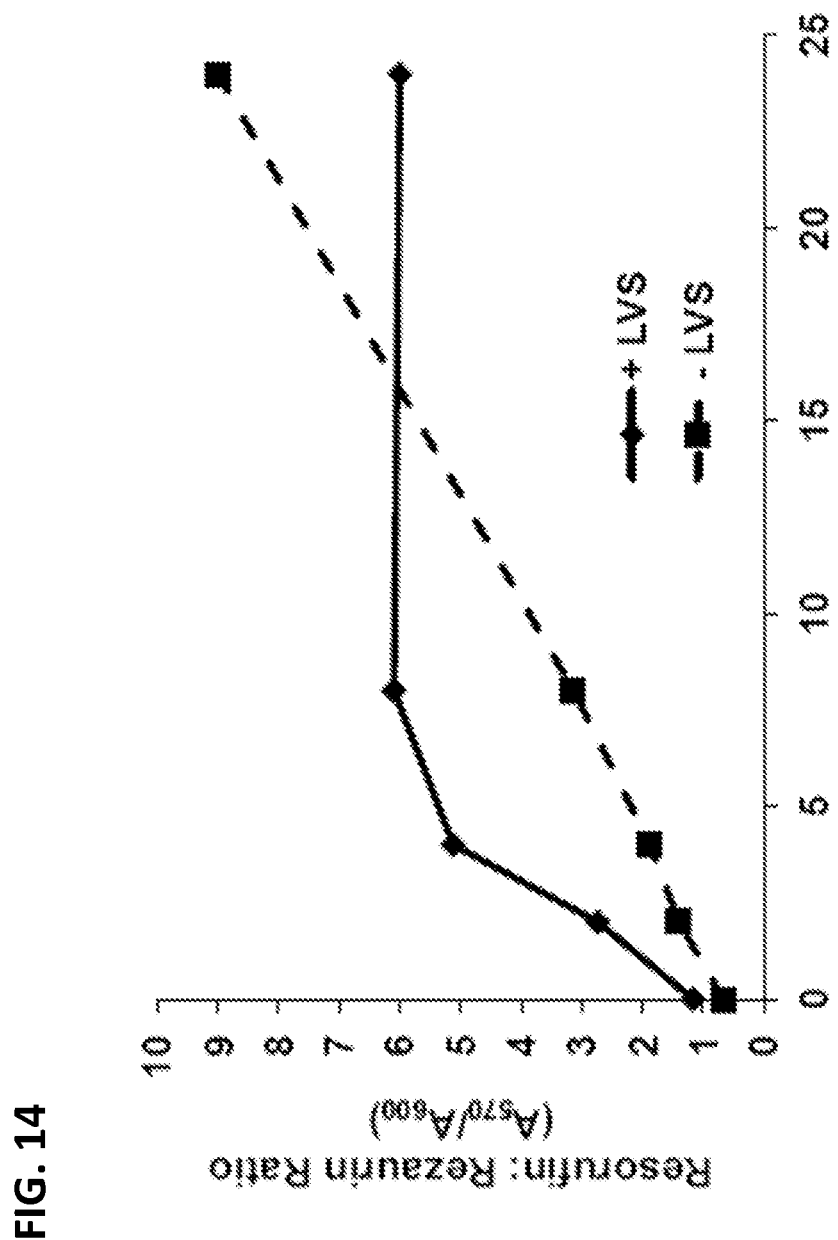

Additionally, many systems are capable of reducing resazurin to resorufin. This reaction would likely occur in a host organism if resazurin were to be used as a treatment. To determine whether this reduction was occurring in *F. tularensis* LVS cultures, the ratio of resorufin to resazurin was measured over time using the optical densities at 570 nm (resorufin) and 600 nm (resazurin). The ratio of resorufin to resazurin increased 3-fold within two hours of inoculation with *F. tularensis* LVS, reaching a maximum ratio of 5 four hours post-inoculation which was maintained for the remainder of the 24 hour period (FIG. 14). This indicated that *F. tularensis* LVS bacteria were reducing resazurin to resorufin.

Figure 10:
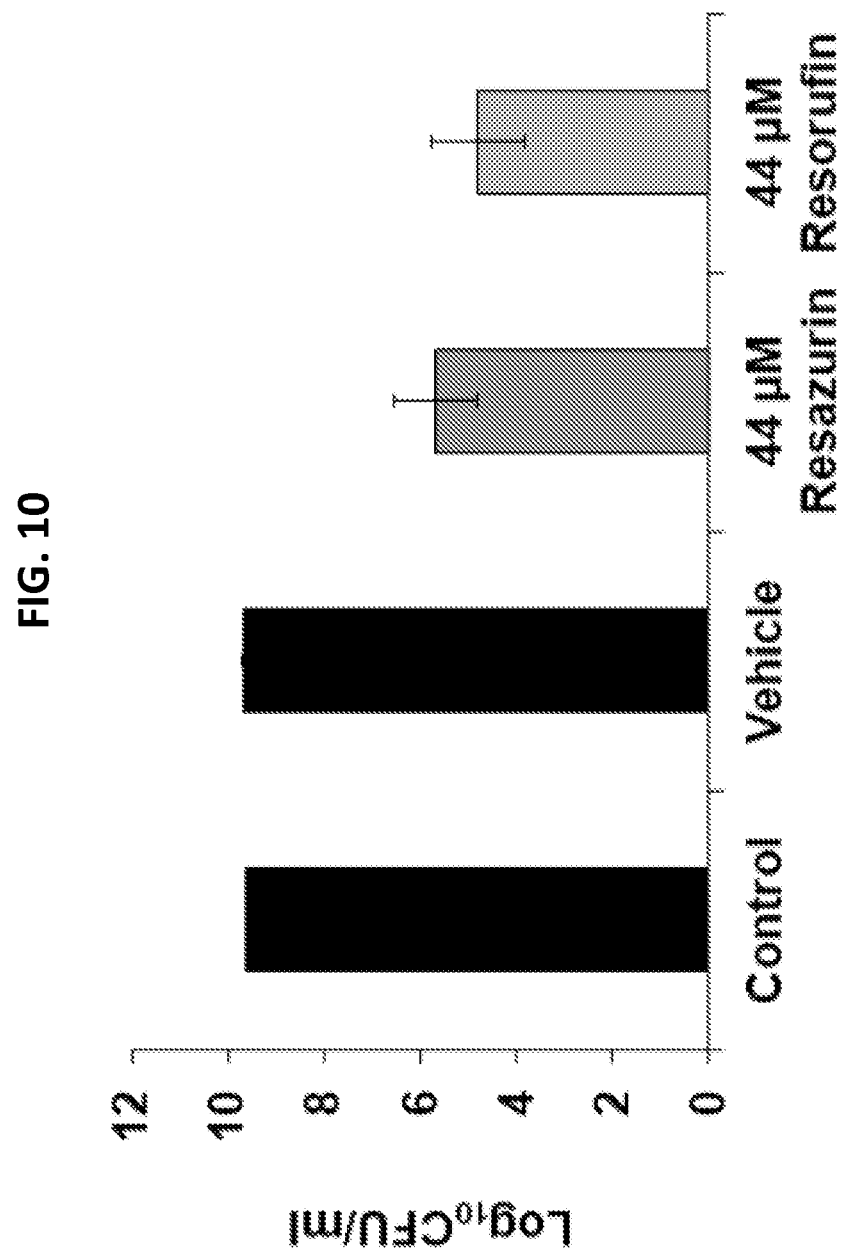
Figure 13:
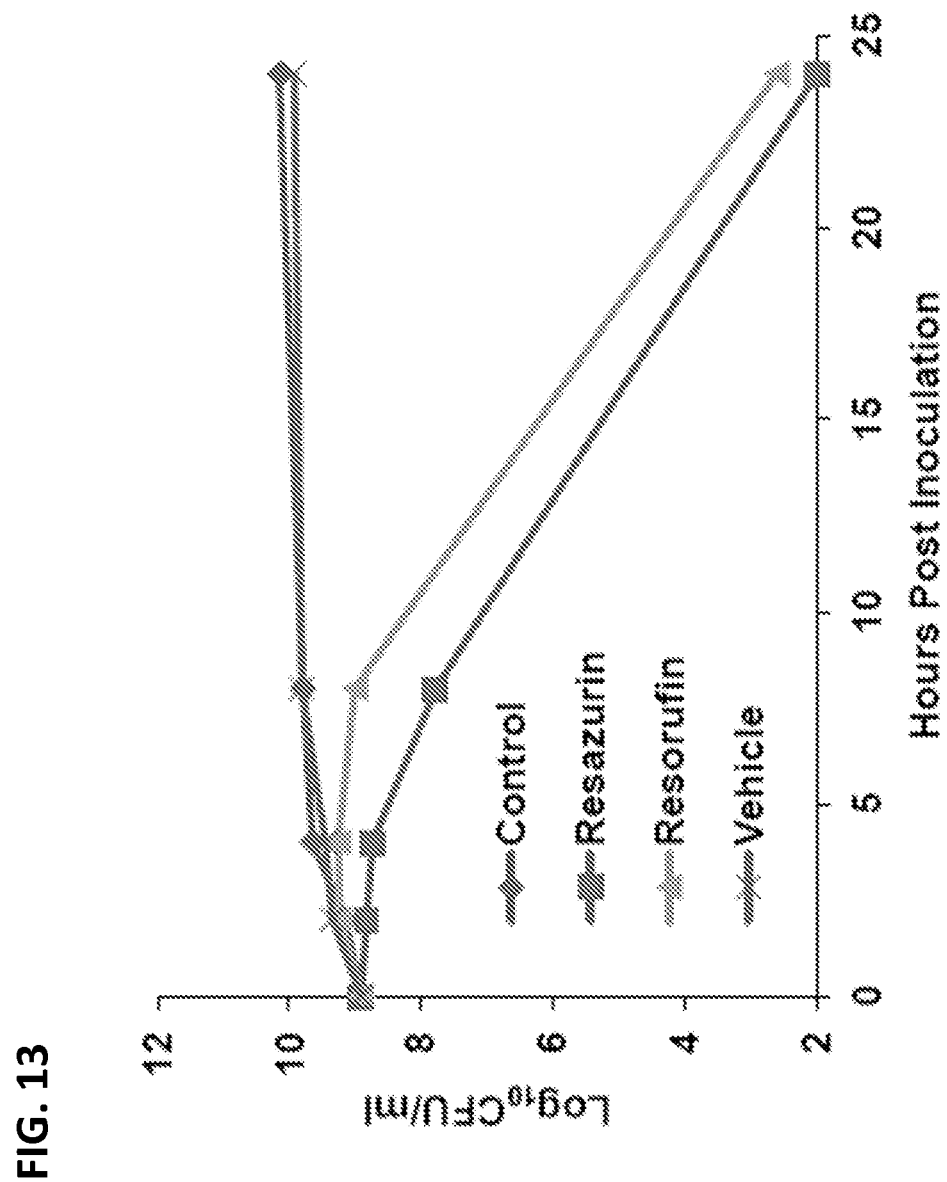

*F. tularensis* LVS bacteria were then incubated with resorufin and evaluated for viability by plating for colony forming units (CFU). The results indicated that resorufin had an equivalently potent antimicrobial effect on *F. tularensis* LVS viability relative to resazurin, indicating that the act of reducing resazurin is not responsible for the observed antimicrobial effect (FIG. 10). This does however indicate that if resazurin were to be used as a therapeutic in an animal, the reduction of this compound by the host's cells would not result in a decrease in the potency of the drug (FIG. 13).

Figure 15:
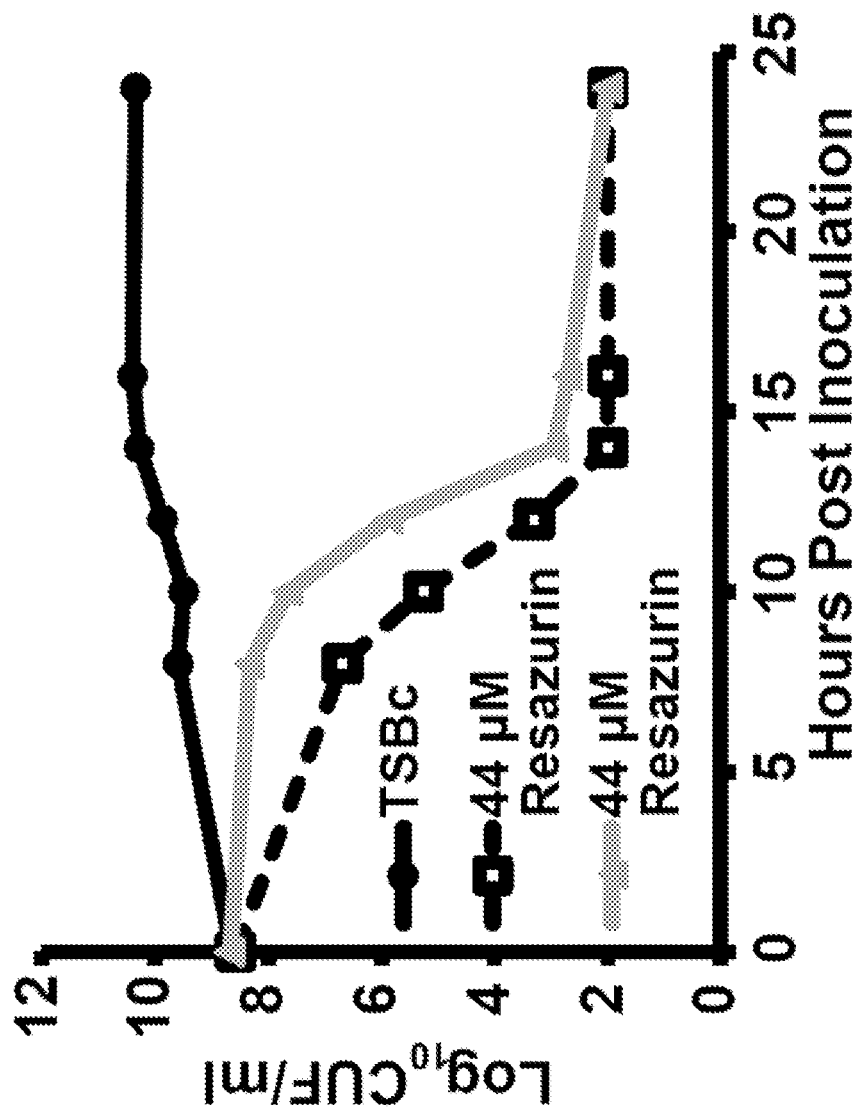

To evaluate whether resazurin must first be converted to resorufin to exhibit antibacterial activity, *F. tularensis* LVS bacteria were grown in the presence of resazurin and resorufin, and the viability over time was measured. In cultures treated with resazurin, reduction of this compound to resorufin was observed as early as two hours post-inoculation (FIG. 14). However, a significant decline in viable bacteria occurred eight hours post-inoculation (FIG. 15). Moreover, a similar decrease in bacterial viability was observed in cultures initially treated with resorufin (FIG. 15). Because resazurin and resorufin both exhibit a similar antimicrobial effect on *F. tularensis*, this indicated that the process of converting resazurin to resorufin was not responsible for the observed bactericidal activity. However, the data indicated that resazurin was rapidly converted to resorufin, while the drop in viability occurred most drastically after 8 hours. This indicated that resorufin was the biologically active form responsible for decreasing the viability of *F. tularensis* LVS bacteria in the culture.

Figure 5:
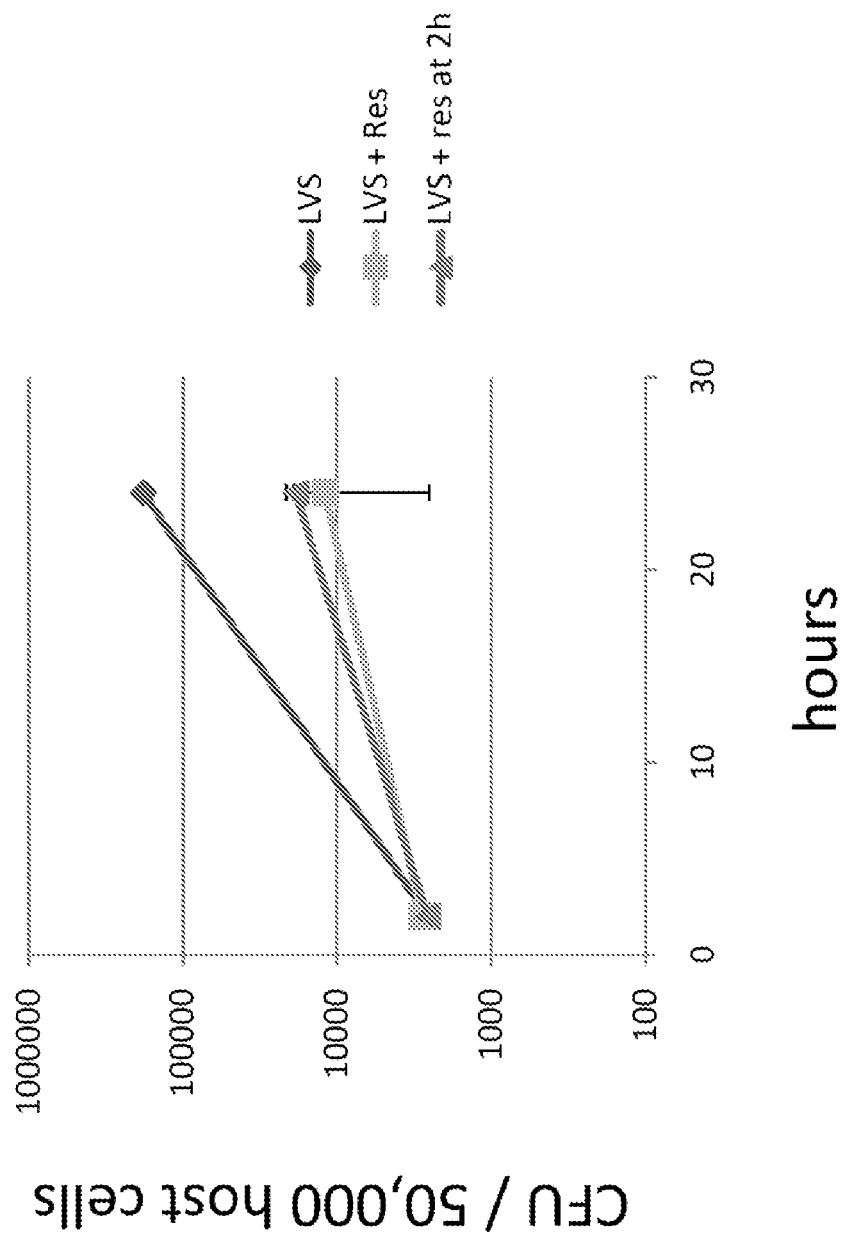

To test the potential of resazurin in an in vitro infection model, primary human macrophages and HEK-293 cells were infected with *F. tularensis* LVS, and viable intracellular bacteria were quantified using a standard gentamicin protection assay. For the primary human macrophages, cells were treated with 44 µM resazurin during the entire assay (+Rz), beginning at two hours post infection (+2 hr Rz), or were untreated. Both resazurin treatments resulted in a substantial decrease in viable bacteria (FIG. 5), suggesting that resazurin could be an effective therapeutic. A visible observation indicated that these macrophages reduced the resazurin to resorufin during this assay, although this phenomenon was not quantified. The reduction of resazurin to resorufin did however indicate that these macrophages were still viable, and that the combination of resazurin and the bacteria did not culminate in undesirable toxicity.

Figure 4:
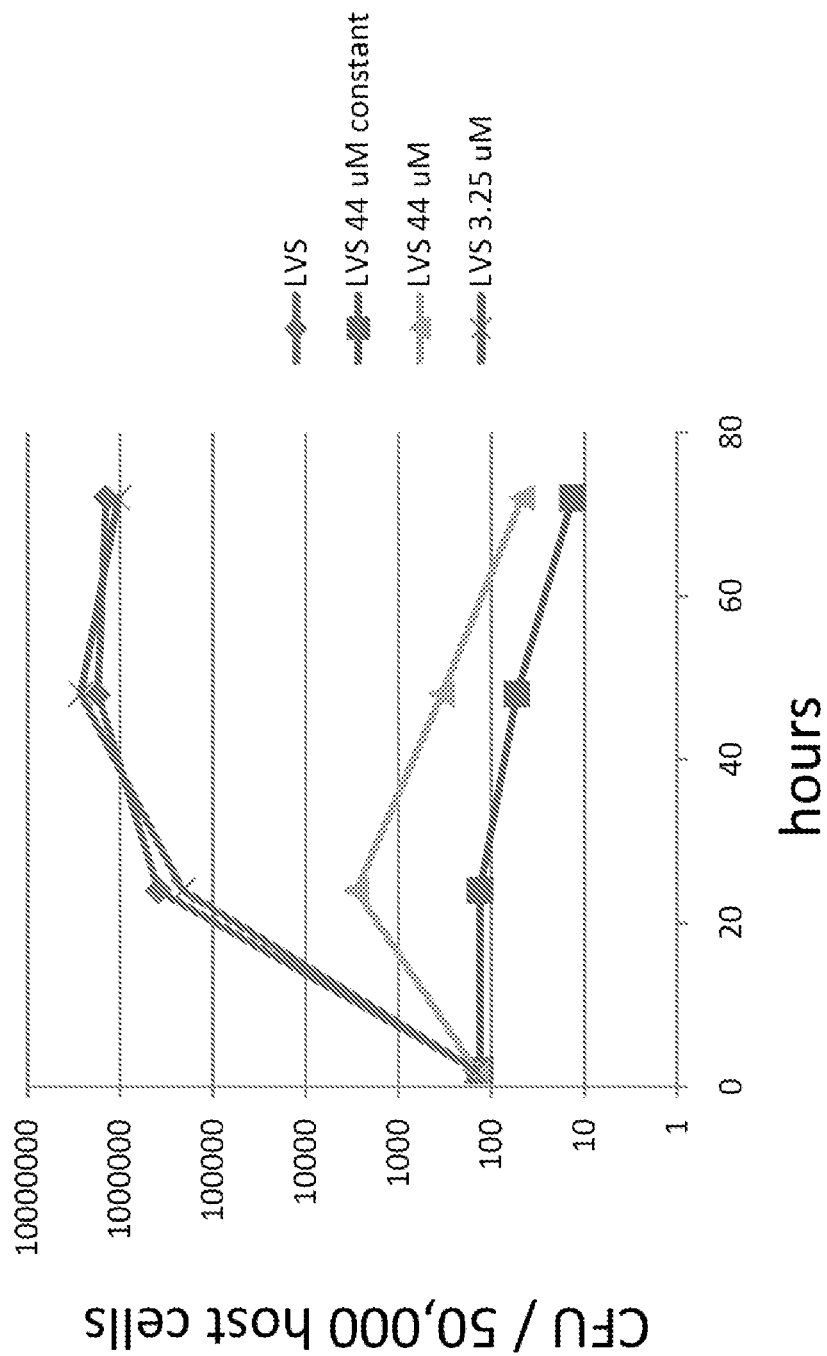

For the HEK-293 cells, 44 µM resazurin was administered at time zero (LVS 44 µM constant), and at 2 hours post infection 44 µM and 3.25 µM was administered (LVS 44 µM and LVS 3.25 µM). Both the 44 µM treatments resulted in a substantial decrease in viable bacteria, compared to the control (FIG. 4).

Figure 11:
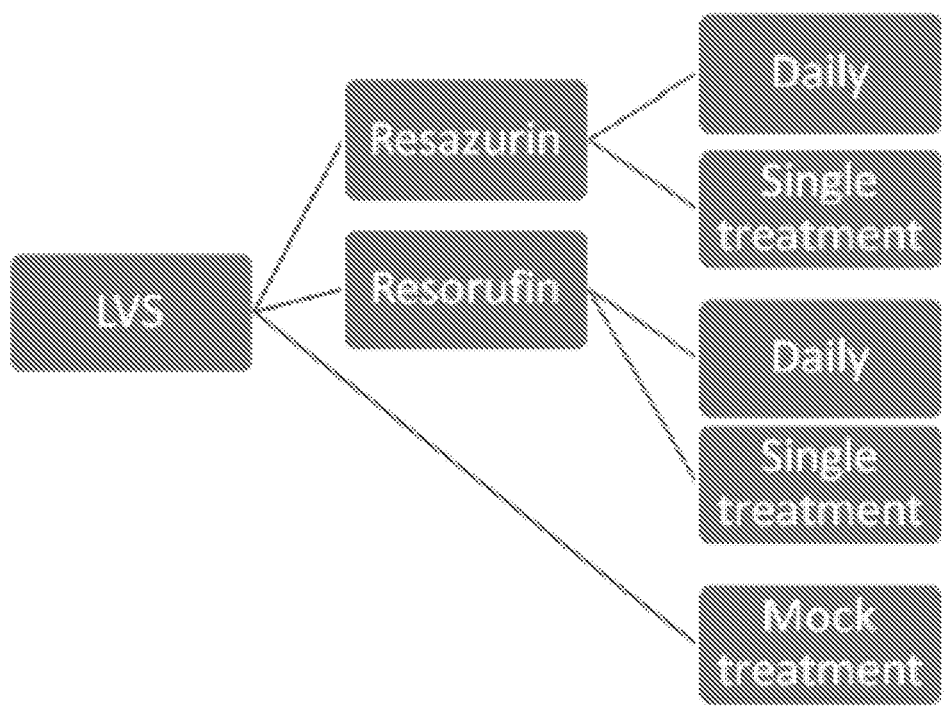
Figure 12:
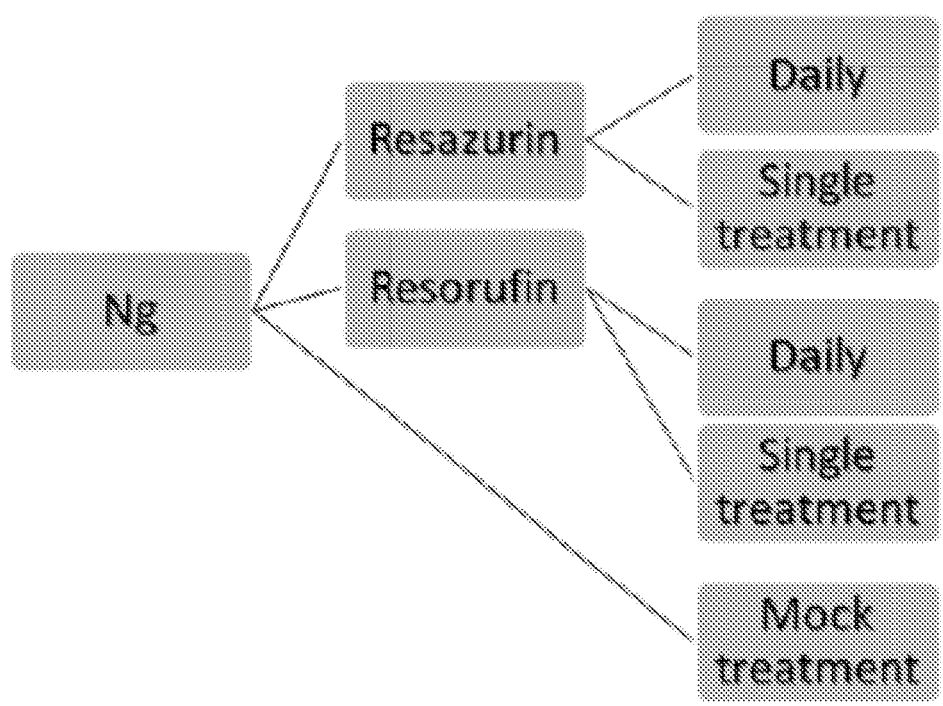

Two in vivo experiments are planned in murine models. These are designed to test resazurin and resorufin as effective therapies for *F. tularensis* or *Neisseria* infections. FIGS. 11 and 12 show the flow charts for the *F. tularensis* and *N. gonorrhoeae* experiments respectively.

To test the drugs against a *F. tularensis* infection, C57BL/6 mice will be infected i.t. with a lethal dose of *F. tularensis* LVS. Subsequently mice will receive a single treatment or daily s.c. injection of resazurin or resorufin (either at 1.1 or 11 mg/kg). A subset of mice will receive a mock treatment (PBS) as a control (FIG. 11).

In the *N. gonorrhoeae* experiment, female BALB/c mice implanted with estradiol will be infected intravaginally with $10^7$ *N. gonorrhoeae* bacteria. Subsequently mice will receive a single treatment or daily s.c. injection of resazurin or resorufin (either at 1.1 or 11 mg/kg), and a subset of mice will receive a mock treatment (PBS) as a control (FIG. 12).

B. Pharmaceutical Compositions

The agents disclosed herein can be included in a pharmaceutical composition for administration to a subject. In particular, disclosed herein are compositions, such as pharmaceutical compositions, for use in treating and/or inhibiting an infection by a pathogen of interest, for use in the manufacture of a medicament, and/or for use as medicament. In some examples, a subject is selected for treatment that has or is at risk for developing an infection by a bacterial pathogen. The agents and compositions disclosed herein may also be used for removing or reducing or preventing bacterial contamination of a substrate such as foodstuff, food processing equipment, food processing plants, surfaces coming into contact with foodstuff, medical devices, and surfaces in hospitals and surgeries.

In one embodiment, the agents described herein may be used for the treatment, amelioration or prevention of a disease induced by or related to a bacterial infection. In one aspect, the term "bacterial infection" refers to transfer, lodgement and penetration of bacteria, respectively, in a macroorganism such as a human, an animal or a plant and propagation of the bacteria or the protozoa in said macroorganism. The meaning of the term "infection" may also be deduced from standard textbooks, such as Pschyrembel (Klinisches Worterbuch, 257. Edition, 1994). A bacterial infection which causes pain or suffering in a subject may generally be considered as "bacterial infectious disease." The treatment, amelioration or prevention of a bacterial infection, as referred to herein, includes the treatment, amelioration or prevention of a disease induced by or related to a bacterial infection. The compound may also be used for the treatment, amelioration and prevention of a bacterial infection even if the infection does not cause pain or suffering in a subject. The agents disclosed herein may also be used against bacterial strains with resistance to antibiotics.

The pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The agents disclosed herein can be administered to subjects by a variety of mucosal administration modes, including by oral, rectal, intranasal, intrapulmonary, or transdermal delivery, or by topical delivery to other surfaces. Optionally, the agents can be administered by non-mucosal routes, including by intramuscular, subcutaneous, intravenous, intra-arterial, intra-articular, intraperitoneal, intrathecal, intracerebroventricular, or parenteral routes. In other alternative embodiments, the agents can be administered ex vivo by direct exposure to cells, tissues or organs originating from a subject.

To formulate the pharmaceutical compositions, the agents can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The agents can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The agents can be combined with the base or vehicle according to a variety of methods, and release of the agents can be by diffusion, disintegration of the vehicle, or associated formation of water channels. In some circumstances, the agent is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the agents can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the agents can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the agent can be delivered to a subject in a manner consistent with conventional methodologies associated with management of the disorder for which treatment or prevention is sought. In accordance with the disclosure herein, a prophylactically or therapeutically effective amount of the agent is administered to a subject in need of such treatment for a time and under conditions sufficient to prevent, inhibit, and/or ameliorate a selected disease or condition or one or more symptom(s) thereof.

The administration of the agent can be for either prophylactic or therapeutic purpose. When provided prophylactically, the agent is provided in advance of any symptom. The prophylactic administration of the agents serves to prevent or ameliorate any subsequent disease process. When provided therapeutically, the compound is provided at (or shortly after) the onset of a symptom of disease or infection.

For prophylactic and therapeutic purposes, the agent can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the agent can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the agents may simply inhibit or enhance one or more selected biological activities correlated with a disease or condition, as set forth herein, for either therapeutic or diagnostic purposes.

The actual dosage of the agents will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the agent for eliciting the desired activity or biological response in the subject. Dosage regimens can be adjusted to provide an optimum prophylactic or therapeutic response. A therapeutically effective amount is also one in which any toxic or detrimental side effects of the agent is outweighed in clinical terms by therapeutically beneficial effects. A non-limiting range for a therapeutically effective amount of an agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight. Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The agents described herein may be used in combination (e.g., co-administered) with one or more antibiotics and/or one or more antiseptics.

Illustrative antibiotics include, for example, tetracycline-derived antibiotics such as, e.g., tetracycline, doxycycline, chlortetracycline, clomocycline, demeclocycline, lymecycline, meclocycline, metacycline, minocycline, oxytetracycline, penimepicycline, rolitetracycline, or tigecycline; amphenicol-derived antiobiotics such as, e.g., chloramphenicol, azidamfenicol, thiamphenicol, or florfenicol; macrolide-derived antiobiotics such as, e.g., erythromycin, azithromycin, spiramycin, midecamycin, oleandomycin, roxithromycin, josamycin, troleandomycin, clarithromycin, miocamycin, rokitamycin, dirithromycin, flurithromycin, telithromycin, cethromycin, tulathromycin, carbomycin A, kitasamycin, midecamicine, midecamicine acetate, tylosin (tylocine), or ketolide-derived antiobiotics such as, e.g., telithromycin, or cethromycin; lincosamide-derived antiobiotics such as, e.g., clindamycin, or lincomycin; streptogramin-derived antiobiotics such as, e.g., pristinamycin, or quinupristin/dalfopristin; oxazolidinone-derived antiobiotics such as, e.g., linezolid, or cycloserine; aminoglycoside-derived antiobiotics such as, e.g., streptomycin, neomycin, framycetin, paromomycin, ribostamycin, kanamycin, amikacin, arbekacin, bekanamycin, dibekacin, tobramycin, spectinomycin, hygromycin B, paromomycin, gentamicin, netilmicin, sisomicin, isepamicin, verdamicin, astromicin, rhodostreptomycin, or apramycin; steroid-derived antiobiotics such as, e.g., fusidic acid, or sodium fusidate; glycopeptide-derived antiobiotics such as, e.g., vancomycin, oritavancin, telavancin, teicoplanin, dalbavancin, ramoplanin, bleomycin, or decaplanin; beta-lactam-derived antiobiotics such as, e.g., amoxicillin, ampicillin, pivampicillin, hetacillin, bacampicillin, metampicillin, talampicillin, epicillin, carbenicillin, carindacillin, ticarcillin, temocillin, azlocillin, piperacillin, mezlocillin, mecillinam, pivmecillinam, sulbenicillin, benzylpenicillin, azidocillin, penamecillin, clometocillin, benzathine benzylpenicillin, procaine benzylpenicillin, phenoxymethylpenicillin, propicillin, benzathine, phenoxymethylpenicillin, pheneticillin, oxacillin, cloxacillin, dicloxacillin, flucloxacillin, meticillin, nafcillin, faropenem, biapenem, doripenem, ertapenem, imipenem, meropenem, panipenem, cefacetrile, cefadroxil, cefalexin, cefaloglycin, cefalonium, cefaloridine, cefalotin, cefapirin, cefatrizine, cefazedone, cefazaflur, cefazolin, cefradine, cefroxadine, ceftezole, cefaclor, cefamandole, cefminox, cefonicid, ceforanide, cefotiam, cefprozil, cefbuperazone, cefuroxime, cefuzonam, cefoxitin, cefotetan, cefmetazole, loracarbef, cefcapene, cefdaloxime, cefdinir, cefditoren, cefetamet, cefixime, cefmenoxime, cefodizime, cefoperazone, cefotaxime, cefpimizole, cefpiramide, cefpodoxime, cefsulodin, ceftazidime, cefteram, ceftibuten, ceftiolene, ceftizoxime, ceftriaxone, flomoxef, latamoxef, cefepime, cefozopran, cefpirome, cefquinome, ceftobiprole, aztreonam, tigemonam, sulbactam, tazobactam, clavulanic acid, ampicillin/sulbactam, sultamicillin, piperacillin/tazobactam, co-amoxiclav, amoxicillin/clavulanic acid, or imipenem/ cilastatin; sulfonamide-derived antiobiotics such as, e.g., acetazolamide, benzolamide, bumetanide, celecoxib, chlorthalidone, clopamide, dichlorphenamide, dorzolamide, ethoxzolamide, furosemide, hydrochlorothiazide, indapamide, mafenide, mefruside, metolazone, probenecid, sulfacetamide, sulfadiazine, sulfadimethoxine, sulfadoxine, sulfanilamides, sulfamethoxazole, sulfamethoxypyridazine, sulfasalazine, sultiame, sumatriptan, xipamide, zonisamide, sulfaisodimidine, sulfamethizole, sulfadimidine, sulfapyridine, sulfafurazole, sulfathiazole, sulfathiourea, sulfamoxole, sulfadimethoxine, sulfalene, sulfametomidine, sulfametoxydiazine, sulfaperin, sulfamerazine, sulfaphenazole, or sulfamazone; quinolone-derived antiobiotics such as, e.g., cinoxacin, flumequine, nalidixic acid, oxolinic acid, pipemidic acid, piromidic acid, rosoxacin, ciprofloxacin, enoxacin, fleroxacin, lomefloxacin, nadifloxacin, ofloxacin, norfloxacin, pefloxacin, rufloxacin, balofloxacin, grepafloxacin, levofloxacin, pazufloxacin, sparfloxacin, temafloxacin, tosufloxacin, besifloxacin, clinafloxacin, garenoxacin, gemifloxacin, moxifloxacin, gatifloxacin, sitafloxacin, trovafloxacin, alatrofloxacin, prulifloxacin, danofloxacin, difloxacin, enrofloxacin, ibafloxacin, marbofloxacin, orbifloxacin, pradofloxacin, sarafloxacin, ecinofloxacin, or delafloxacin; imidazole-derived antiobiotics such as, e.g., metronidazole; nitrofuran-derived antiobiotics such as, e.g., nitrofurantoin, or nifurtoinol; aminocoumarin-derived antiobiotics such as, e.g., novobiocin, clorobiocin, or coumermycin A1; ansamycin-derived antiobiotics, including rifamycin-derived antiobiotics such as, e.g., rifampicin (rifampin), rifabutin, rifapentine, or rifaximin; and also further antiobiotics such as, e.g., fosfomycin, bacitracin, colistin, polymyxin B, daptomycin, xibornol, clofoctol, methenamine, mandelic acid, nitroxoline, mupirocin, trimethoprim, brodimoprim, iclaprim, tetroxoprim, or sulfametrole; without being limited thereto.

Illustrative antiseptics include, for example, acridine-derived antiseptics such as, e.g., ethacridine lactate, aminoacridine, or euflavine; amidine-derived or biguanide-derived antiseptics such as, e.g., dibrompropamidine, chlorhexidine, propamidine, hexamidine, or polihexanide; phenol-derived antiseptics such as, e.g., phenol, hexachlorophene, policresulen, triclosan, chloroxylenol, or biphenylol; nitrofuran-derived antiseptics such as, e.g., nitrofurazone; iodine-based antiseptics such as, e.g., iodine/octylphenoxypolyglycolether, povidone-iodine, or diiodohydroxypropane; quinolone-derived antiseptics such as, e.g., dequalinium, chlorquinaldol, oxyquinoline, or clioquinol; quaternary ammonium-derived antiseptics such as, e.g., benzalkonium, cetrimonium, cetylpyridinium, cetrimide, benzoxonium chloride, or didecyldimethylammonium chloride; mercurial antiseptics such as, e.g., mercuric amidochloride, phenylmercuric borate, mercuric chloride, mercurochrome, thiomersal, or mercuric iodide; silver-based antiseptics such as, e.g., silver nitrate; alcoholic antiseptics such as, e.g., propanol (including isopropanol), or ethanol; and also further antiseptics such as, e.g., potassium permanganate, sodium hypochlorite, hydrogen peroxide, eosin, tosylchloramide sodium, dichlorobenzyl alcohol, ambazone, benzethonium, myristyl-benzalkonium, hexylresorcinol, or acriflavinium chloride; without being limited thereto.

Co-therapy using the agents disclosed herein with other antibiotic(s) and/or antiseptic(s) may result in a synergistic effect, i.e. the agents acting together may create an effect greater than that predicted by knowing only the separate effects of the individual agents. Such a synergistic effect might be particularly advantageous if less amounts of the agent(s), antibiotic(s) and/or antiseptic(s) may then be used. Thus, possible side-effects of the compound(s), antibiotic(s) and/or antiseptic(s) might be diminished or avoided.

Examples

Resazurin was bactericidal for *F. tularensis, N. polysaccharea, N. sicca*, and *F. novicida* when they were cultivated in synthetic media with resazurin at concentrations that are not toxic to mammalian cells (see FIGS. 1-3). Further investigation with *F. tularensis* indicated that resazurin inhibited intracellular growth of this pathogen in HEK-293 cells and primary human macrophages (see FIGS. 4 and 5).
Materials and Methods
Inhibition of Bacterial Growth on Chocolate II Agar.

Bacteria were plated by quadrant streak onto chocolate II agar (GC Agar supplemented with hemoglobin and IsoVitaleX) with or without 44 µM resazurin and incubated at 37° C. Bacterial growth was observed daily for up to three days. No observable inhibition of growth was scored as "+" where qualitative growth inhibition was scored as "−". See FIG. 1.
Resazurin is Bactericidal to *F. tularensis* in Broth Culture.

Trypticase soy broth supplemented with 0.1% cysteine HCl (TSBc) was supplemented with various concentrations of resazurin, and OD600 was measured after incubation overnight at 37° C. with agitation. A normalized amount of *Francisella tularensis* LVS bacteria was used to inoculate broth cultures (either TSBc or Chamberlains' chemically defined medium [CDM]) with or without 44 µM resazurin. At the indicated times, OD600 was measured and bacteria were enumerated by plating serial dilutions. See FIG. 3.
In Vitro Infections.

HEK-293 cells or primary human macrophages were infected with *F. tularensis* LVS, and intracellular CFU were measured using a gentamicin protection assay. For infection of HEK-293 cells, resazurin was administered at time 0 (LVS 44 µM constant) or at 2 h post-infection (LVS 44 µM, LVS 3.25 µM). For the human macrophage infections, 44 µM resazurin was added at time 0 (LVS+Res) or at 2 h post-infection (res at 2 h). See FIG. 4.
Resorufin is Bactericidal to *F. tularensis* in Broth Culture.

Figure 6:
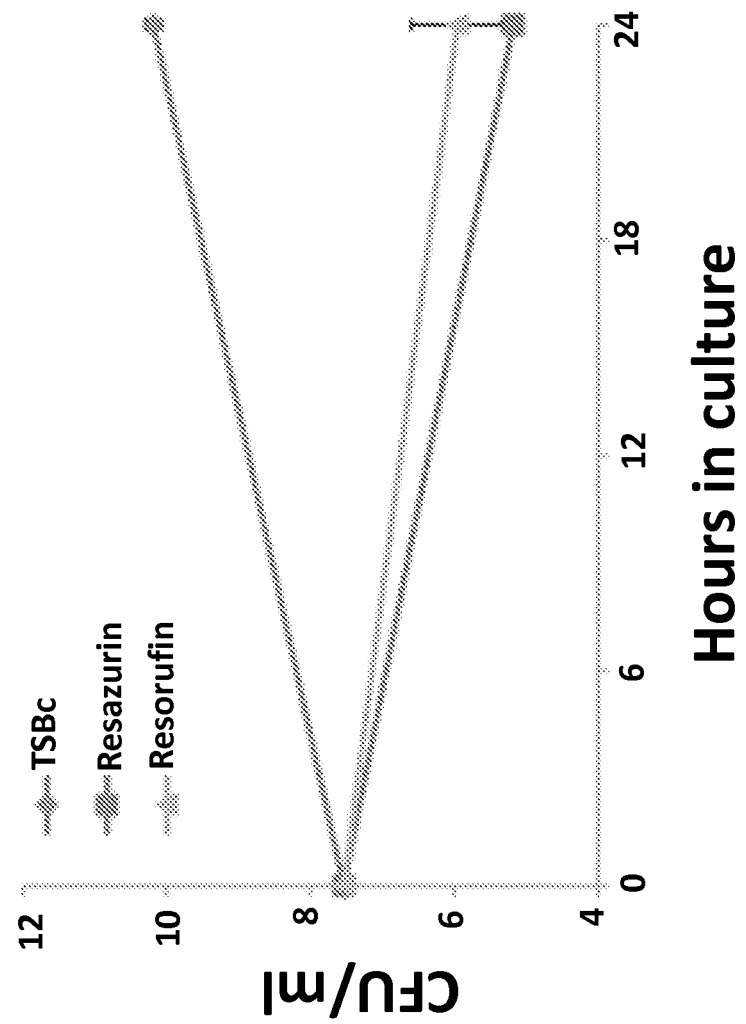

Trypticase soy broth supplemented with 0.1% cysteine HCl (TSBc) was supplemented with or without 44 µM resazurin or resorufin, and the number of viable bacteria per ml was measured after incubation overnight at 37° C. with agitation. A normalized amount of *Francisella tularensis* LVS bacteria was used to inoculate broth cultures in TSBc with or without 44 µM resazurin or resorufin. At the indicated times bacteria were enumerated by plating serial dilutions. The results indicate that resazurin and resorufin have antibacterial activity against *Francisella tularensis* (see FIG. 6).
Reduction of Resazurin to Resorufin by *F. tularensis*.

*F. tularensis* was cultured in TSBc supplemented with 44 µM resazurin at 37° C. with shaking for 24 hours. At select timepoints, a Spectronic 200 Spectrophotometer was used to measure the absorbance at 600 nm and 570 nm to detect the presence of resazurin and resorufin respectively. The ratio of these two optical densities was used to evaluate reduction of resazurin to resorufin over time. The results indicated that the ratio of resorufin to resazurin increased 3-fold within two hours of inoculation with *F. tularensis* LVS and reached a maximum ratio of 5 four hours post-inoculation. This level was maintained for the remainder of the 24 hour period (FIG. 14). This result indicated that *F. tularensis* LVS does reduce resazurin to resorufin.

In Vivo Assay, to Test Resazurin and Resorufin as Therapies for Tularemia.

Murine models of pulmonary tularemia will be utilized. Importantly, only *F. tularensis* LVS will be used to infect mice for the work described herein. This organism is a BSL2 bacterium, is not a human pathogen, and is exempt from the select agent list. The overall research plan proposed for this test can be seen in FIG. 11. Mice (C57BL/6) will be infected with a lethal dose of *F. tularensis* LVS via intratracheal instillation (i.t.). Briefly, anesthetized mice will be suspended by their front incisors, and their tongues will be extended with forceps. A suspension of bacteria will be placed at the base of their oropharynx, and subsequently the mice will aspirate this fluid. On day one post infection, mice will be treated with resazurin or resorufin (both at 1.1 or 11 mg/kg) by subcutaneous injection (s.c). This dose is based on the MIC values calculated in vitro (FIG. 9). A subset of mice will get daily treatments of resazurin or resorufin at the dose they received on day one. A control group of mice will be infected and mock treated (PBS). Mice will be monitored for signs of morbidity or mortality. Based on our in vitro data, substantial survival is expected in the treatment groups relative to untreated infected mice.

In Vivo Assay, to Test Resazurin and Resorufin as Therapies for Gonorrhea.

The mouse gonorrhea model will be used to test the therapeutic efficacy of resazurin and resorufin in vivo. The overall research plan proposed for this test can be seen in FIG. 12. A 5-mg, 21-day controlled-release estradiol pellet (Research of America, Sarasota, Fla.) will be injected intradermally into 6-8 week old female BALB/c mice during diestrus. Diestrus will be determined by observing vaginal smears prepared on glass slides, and staining with Hema-3. The treatment with estradiol is essential for vaginal colonization by *N. gonorrhoeae*. As overgrowth of commensal flora occurs during estradiol treatment, mice will receive an antibiotic regimen that consists of streptomycin sulfate (1.2 mg) and vancomycin HCl (0.6 mg) twice daily via intraperitoneal injection. In addition, mice will be fed drinking water containing trimethoprim sulfate (0.04 g/100 ml of drinking water). Antibiotic injections will cease prior to infection (48 h before infection for streptomycin and 24 h for vancomycin), however, trimethoprim will remain in the drinking water throughout the experiment. Two days after the estradiol pellet implantation, mice will be anesthetized with ketamine and xylazine and infected intravaginally (using a micropipette) with $10^7$ CFU of *N. gonorrhoeae* suspended in 20 pl of PBS. On day one post infection, mice will be treated with resazurin or resorufin (both at 1.1 or 11 mg/kg) s.c. A subset of mice will get daily treatments of resazurin or resorufin at the dose they received on day one post infection. A control group of mice will be infected, but will be mock treated with PBS. Vaginal secretion will be collected from mice daily with a sterile swab and will be suspended in 50 pl of saline. Bacteria will be recovered from each mouse by plating undiluted or serial dilutions of vaginal secretions on GCVCNT agar (contains an antibiotic mixture of vancomycin, colistin, nystatin, and trimethoprim to select and isolate *Neisseria* from the vagina). A significant reduction in viable *N. gonorrhoeae* bacteria from mice treated with resazurin or resorufin is expected relative to untreated mice.

In view of the many possible embodiments to which the principles of the disclosed invention may be applied, it should be recognized that the illustrated embodiments are only preferred examples of the invention and should not be taken as limiting the scope of the invention.

We claim:

1. A method for treating infection by bacteria in a subject, comprising administering to the subject a therapeutically effective amount of a compound selected from resazurin, resorufin, a compound of formula II, or a compound of formula IV, or a pharmaceutically acceptable salt or ester thereof, and wherein the bacteria is selected from at least one of *Francisella* sp. or *Neisseria* sp., and the compound of formula II has a structure of:

or a pharmaceutically acceptable salt or ester thereof;
where $R^2$, $R^3$, $R^4$, $R^5$, $R^6$ and $R^7$ are each independently hydrogen;
A is $OR^8$;
Z is O;
X is oxygen; and
$R^8$ is alkyl, aralkyl, alkylaryl, or hydrogen; and
the compound of formula IV has a structure of:

or a pharmaceutically acceptable salt or ester thereof;
where $R^2$, $R^3$, $R^4$, $R^5$, $R^6$ and $R^7$ are each independently hydrogen;
A is $OR^8$;
Z is O;
X is oxygen; and
$R^8$ is alkyl, aralkyl, alkylaryl, or hydrogen.

2. The method of claim 1, wherein the compound is resazurin or a pharmaceutically acceptable salt or ester thereof.

3. The method of claim 1, wherein $R^8$ is selected from $C_1$-$C_6$ alkyl, aralkyl or alkylaryl.

4. The method of claim 1, wherein the bacteria is selected from *F. tularensis*, *F. novicida*, *N. polysaccharea*, *N. sicca*, *N. gonorrhoeae*, *N. meningitides*, *N. bacilliformis*, *N. cinerea*, *N. elongate*, *N. flavescens*, *N. lactamica*, *N. macacae*, *N. mucosa*, or *N. subflava*.

5. The method of claim 1, wherein $R^8$ is alkyl.

6. The method of claim 1, wherein the bacteria is selected from *F. tularensis* or *N. gonorrhoeae*.

7. The method of claim 6, wherein $R^8$ is alkyl.

8. The method of claim 1, wherein $R^8$ is $C_1$-$C_6$ alkyl.

9. The method of claim 6, wherein $R^8$ is $C_1$-$C_6$ alkyl.

10. A method for inhibiting bacteria growth, comprising contacting an effective amount of a compound selected from resazurin, resorufin, or a compound of formula II, or a compound of formula IV, or a pharmaceutically acceptable salt or ester thereof, with at least one of *Francisella* sp. or *Neisseria* sp., wherein the compound of formula II has a structure of:

or a pharmaceutically acceptable salt or ester thereof;

where $R^2$, $R^3$, $R^4$, $R^5$, $R^6$ and $R^7$ are each independently hydrogen;

A is $OR^8$;

Z is O;

X is oxygen; and $R^8$ is alkyl, aralkyl, alkylaryl, or hydrogen; and the compound of formula IV has a structure of:

or a pharmaceutically acceptable salt or ester thereof;

where $R^2$, $R^3$, $R^4$, $R^5$, $R^6$ and $R^7$ are each independently hydrogen;

A is $OR^8$;

Z is O;

X is oxygen; and $R^8$ is alkyl, aralkyl, alkylaryl, or hydrogen.

11. The method of claim 10, wherein the compound is resorufin, or a pharmaceutically acceptable salt or ester thereof.

12. The method of claim 10, wherein the compound has a formula

III:

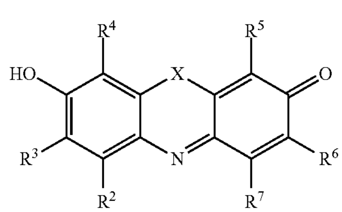

or a pharmaceutically acceptable salt or ester thereof.

13. The method of claim 10, wherein the compound is resazurin or a pharmaceutically acceptable salt or ester thereof.

14. A method for inhibiting the growth of at least one of *Francisella* sp. or *Neisseria* sp. on a substrate, comprising contacting the substrate with a compound selected from resazurin, resorufin, or a compound of formula II, or a compound of formula IV, or a pharmaceutically acceptable salt or ester thereof, wherein the compound of formula II has a structure of:

or a pharmaceutically acceptable salt or ester thereof;

where $R^2$, $R^3$, $R^4$, $R^5$, $R^6$ and $R^7$ are each independently hydrogen;

A is $OR^8$;

Z is O;

X is oxygen; and $R^8$ is alkyl, aralkyl, alkylaryl, or hydrogen; and the compound of formula IV has a structure of:

or a pharmaceutically acceptable salt or ester thereof;

where $R^2$, $R^3$, $R^4$, $R^5$, $R^6$ and $R^7$ are each independently hydrogen;

A is $OR^8$;

Z is O;

X is oxygen; and $R^8$ is alkyl, aralkyl, alkylaryl, or hydrogen.

15. The method of claim 14, wherein the compound is resorufin, or a pharmaceutically acceptable salt or ester thereof.

16. The method of claim 14, wherein the compound is resazurin or a pharmaceutically acceptable salt or ester thereof.

17. The method of claim 14, wherein $R^8$ is alkyl.

* * * * *